(12) United States Patent
Bernasconi et al.

(10) Patent No.: US 10,179,189 B2
(45) Date of Patent: *Jan. 15, 2019

(54) THERMOFORMED POLY-4-HYDROXYBUTYRATE MEDICAL IMPLANTS

(71) Applicant: Tepha, Inc., Lexington, MA (US)

(72) Inventors: Matthew Bernasconi, Norwood, MA (US); Dennis Connelly, Arlington, MA (US); Said Rizk, Windham, NH (US); David P. Martin, Arlington, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,975

(22) Filed: May 19, 2017

(65) Prior Publication Data

US 2017/0252481 A1 Sep. 7, 2017

Related U.S. Application Data

(62) Division of application No. 14/464,105, filed on Aug. 20, 2014, now Pat. No. 9,687,585.

(60) Provisional application No. 61/867,991, filed on Aug. 20, 2013.

(51) Int. Cl.
| | | |
|---|---|---|
| *A61L 27/00* | (2006.01) |
| *A61L 31/00* | (2006.01) |
| *A61L 27/18* | (2006.01) |
| *B29C 51/00* | (2006.01) |
| *B29C 51/42* | (2006.01) |
| *A61L 31/06* | (2006.01) |
| *A61L 27/48* | (2006.01) |
| *A61L 27/50* | (2006.01) |
| *A61L 27/54* | (2006.01) |
| *A61L 31/12* | (2006.01) |
| *A61L 31/14* | (2006.01) |
| *A61L 31/16* | (2006.01) |
| *B29K 67/00* | (2006.01) |
| *B29L 31/00* | (2006.01) |

(52) U.S. Cl.
CPC ............... *A61L 27/18* (2013.01); *A61L 27/48* (2013.01); *A61L 27/50* (2013.01); *A61L 27/54* (2013.01); *A61L 31/06* (2013.01); *A61L 31/129* (2013.01); *A61L 31/14* (2013.01); *A61L 31/16* (2013.01); *B29C 51/002* (2013.01); *B29C 51/421* (2013.01); *A61L 2430/34* (2013.01); *B29K 2067/04* (2013.01); *B29K 2995/0056* (2013.01); *B29L 2031/753* (2013.01); *B29L 2031/7532* (2013.01); *Y10T 428/31786* (2015.04); *Y10T 442/164* (2015.04)

(58) Field of Classification Search
CPC .......... A61L 27/18; A61L 27/48; A61L 31/06; A61L 31/129; A61L 27/50; A61L 27/54; A61L 31/14; A61L 31/16; B29C 51/002; B29C 51/421

See application file for complete search history.

(56) References Cited

U.S. PATENT DOCUMENTS

| | | |
|---|---|---|
| 5,811,272 A | 9/1998 | Snell |
| 5,834,582 A | 11/1998 | Sinclair |
| 6,245,537 B1 | 6/2001 | Williams |
| 6,316,262 B1 | 11/2001 | Huisman |
| 6,323,010 B1 | 11/2001 | Skraly |
| 6,548,569 B1 | 4/2003 | Williams ............. C08K 5/0033 521/27 |
| 6,555,123 B2 | 4/2003 | Williams |
| 6,585,994 B2 | 7/2003 | Williams |
| 6,610,764 B1 | 8/2003 | Martin |
| 6,623,748 B2 | 9/2003 | Clokie |
| 6,828,357 B1 | 12/2004 | Martin |
| 6,838,493 B2 | 1/2005 | Williams |
| 6,867,247 B2 | 3/2005 | Williams |
| 6,867,248 B1 | 3/2005 | Martin |
| 6,878,758 B2 | 4/2005 | Signer |
| 7,025,980 B1 | 4/2006 | Williams |

(Continued)

FOREIGN PATENT DOCUMENTS

| | | |
|---|---|---|
| EP | 1136510 | 9/2001 |
| WO | 1999032536 | 7/1999 |

(Continued)

OTHER PUBLICATIONS

Martin et al., Medical applications of poly-4-hydroxybutyrate: a strong flexible absorbable biomaterial. Biochemical Engineering Journal (2003) 16:97-105.

(Continued)

*Primary Examiner* — Robert A Wax
*Assistant Examiner* — Olga V Tcherkasskaya
(74) *Attorney, Agent, or Firm* — Pabst Patent Group LLP

(57) ABSTRACT

Methods to produce thermoforms from P4HB homopolymer and blends thereof have been developed. These thermoforms are produced from films and sheets including P4HB, wherein the intrinsic viscosity of the P4HB is less than 3.5 dl/g, but greater than 0.35 dl/g, and the thermoforms are produced at a temperature equal to or greater than the softening point of P4HB, and more preferably at a temperature higher than the melting point of P4HB. A preferred embodiment includes a P4HB thermoform wherein a film or sheet including a P4HB polymer is thermoformed at a temperature between its melting point and 150° C. In a particularly preferred embodiment the thermoform is a laminate made from a P4HB film and a P4HB mesh.

13 Claims, 1 Drawing Sheet

(56) References Cited

U.S. PATENT DOCUMENTS

| | | |
|---|---|---|
| 7,179,883 B2 | 2/2007 | Williams |
| 7,244,442 B2 | 7/2007 | Williams |
| 7,268,205 B2 | 9/2007 | Williams |
| 7,553,923 B2 | 6/2009 | Williams |
| 7,618,448 B2 | 11/2009 | Schmitz |
| 7,641,825 B2 | 1/2010 | Rizk |
| 7,678,444 B2 | 3/2010 | Tedford, Jr. ............ B32B 1/02 264/173.11 |
| 7,943,683 B2 | 5/2011 | Rizk ............ A61L 27/18 264/177.17 |
| 8,016,883 B2 | 9/2011 | Coleman |
| 8,034,270 B2 | 10/2011 | Martin |
| 8,039,237 B2 | 10/2011 | Martin |
| 8,227,060 B2 | 7/2012 | Obuchi |
| 8,231,889 B2 | 7/2012 | Williams |
| 8,287,909 B2 | 10/2012 | Martin |
| 2007/0182041 A1 | 8/2007 | Rizk ............ A61L 17/12 264/6 |
| 2008/0132602 A1 | 6/2008 | Rizk ............ A61L 27/18 523/113 |
| 2009/0274920 A1 | 11/2009 | Li ............ B32B 1/02 428/481 |
| 2013/0309166 A1 | 11/2013 | Rizk |
| 2014/0030422 A1 | 1/2014 | Trollsas |

FOREIGN PATENT DOCUMENTS

| | | |
|---|---|---|
| WO | 200056376 | 9/2000 |
| WO | 2007092417 | 8/2007 |
| WO | 2008070428 | 6/2008 |
| WO | 2009137730 | 11/2009 |
| WO | 2011071666 | 6/2011 |
| WO | 2011119743 | 9/2011 |
| WO | 2011159784 | 12/2011 |
| WO | 2012064526 | 5/2012 |

OTHER PUBLICATIONS

William et al. Poly-4-hydroxybutyrate (P4HB): a new generation of resorbable medical devices for tissue repair and regeneration. Biomed Tech (Berl). 2013, 58(5):439-452 (online Jun. 17, 2013).

Hori, et al., "Chemical synthesis of high molecular weight poly(3-hydroxybutyrate-co-4-hydroxybutyrate)". Polymer 36:4703-5 (1995).

Houk, et al., "Why delta-valerolactone polymerizes and gamma-butyrolactone does not", J. Org. Chem., 73 (7), 2674-8 (2008).

Moore, et al., "Chemosynthesis of bioresorbable poly(gamma-butyrolactone) by ring-opening polymerisation: a review", Biomaterials, 26:3771-82 (2005).

Steinbuchel, et al., "Diversity of Bacterial Polyhydroxyalkanoic Acids", FEMS Microbial. Lett. 128:219-28 (1995).

Williams, et al., "Applications of PHAs in Medicine and Pharmacy, in Biopolymers", Polyesters, III, 4:91-127 (2002).

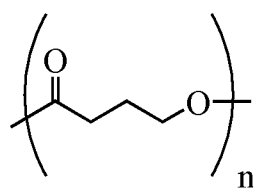

THERMOFORMED POLY-4-HYDROXYBUTYRATE MEDICAL IMPLANTS

CROSS-REFERENCE TO RELATED APPLICATIONS

This application is a divisional of U.S. Ser. No. 14/464,105, filed Aug. 20, 2014, which claims the benefit of and priority to U.S. Ser. No. 61/867,991, filed on Aug. 20, 2013, the disclosures of which are incorporated herein by reference.

FIELD OF THE INVENTION

The present invention generally relates to thermoforming of poly-4-hydroxybutyrate, the compositions used to produce these thermoforms, and the processes used to produce these thermoforms, as well as their use in many types of implant applications including wound management, general surgery including hernia repairs and anti-adhesion devices, tissue engineering, plastic and reconstructive surgery, drug delivery, pelvic floor reconstruction, nerve repair, orthopedic surgery, stenting, periodontal surgery, oral surgery, and vascular and cardiovascular surgery.

BACKGROUND OF THE INVENTION

Thermoforming is a manufacturing process where a plastic sheet is heated to a pliable forming temperature, formed to a specific shape in a mold, and trimmed to create a usable product. The sheet, or "film" when referring to thinner gauges and certain material types, is heated in an oven to a high-enough temperature that it can be stretched into or onto a mold and cooled to a finished shape. In its simplest form, a small tabletop or lab size machine can be used to heat small cut sections of plastic sheet and stretch it over a mold using vacuum. This method is often used for sample and prototype parts. In complex and high-volume applications, very large production machines are utilized to heat and form the plastic sheet and trim the formed parts from the sheet in a continuous high-speed process, and can produce many thousands of finished parts per hour depending on the machine and mold size and the size of the parts being formed. Thermoforming differs from injection molding, blow molding, rotational molding, and other forms of processing plastics. Thin-gauge thermoforming is primarily the manufacture of disposable cups, containers, lids, trays, blisters, clamshells, and other products for the food, medical, and general retail industries. Thick-gauge thermoforming includes parts as diverse as vehicle door and dash panels, refrigerator liners, utility vehicle beds, and plastic pallets. In the most common method of high-volume, continuous thermoforming of thin-gauge products, plastic sheet is fed from a roll or from an extruder into a set of indexing chains that incorporate pins, or spikes, that pierce the sheet and transport it through an oven for heating to forming temperature. The heated sheet then indexes into a form station where a mating mold and pressure-box close on the sheet, with vacuum then applied to remove trapped air and to pull the material into or onto the mold along with pressurized air to form the plastic to the detailed shape of the mold. After a short form cycle, a burst of reverse air pressure is actuated from the vacuum side of the mold as the form tooling opens, commonly referred to as air-eject, to break the vacuum and assist the formed parts off of, or out of, the mold. A stripper plate may also be utilized on the mold as it opens for ejection of more detailed parts or those with negative-draft, undercut areas. The sheet containing the formed parts then indexes into a trim station on the same machine, where a die cuts the parts from the remaining sheet web, or indexes into a separate trim press where the formed parts are trimmed. The sheet web remaining after the formed parts are trimmed is typically wound onto a take-up reel or fed into an inline granulator for recycling.

Each polymer has different properties. Not every polymer is suitable for thermoforming. Amorphous polymers are preferred, melt temperatures are critical, physical properties significantly impact the resulting products. The most common materials that are used are thermoplastics such as polypropylene.

There is a need for biodegradable, strong and flexible polymers that can be processed by thermoforming. WO 2007/092417 to Rizk discloses compositions of polylactic acid ("PLA") toughened with P4HB that have desirable properties for thermoforming, but PLA is relatively inflexible. WO 2011/071666 to Wel discloses methods to make thermoformable compositions of PHA and PLA by cross-linking, including P4HB crosslinked with PLA. WO 2009/137730 to Uradnisheck discloses PHA compositions for thermoforming, including PHAs containing 4-hydroxybutyrate monomers, methods to thermoform PHAs with glass transition temperatures of approximately 55° C. and melting points of around 155° C., and methods to heat-treat finished articles at 105° C., or methods to heat-treat the low melting point P4HB polymer and thermoforms of P4HB. U.S. Pat. No. 5,834,582 to Sinclair discloses compositions of degradable materials and nontoxic modifiers that can be thermoformed. EP 1136510 to Datta and Siegmann discloses a very long list of bioabsorbable polymers, including a polymer of hydroxybutyrate (the common name for poly-3-hydroxybutyrate), which can be thermoformed.

P4HB has entirely different properties compared to P3HB ("PHB"), PLA and copolymers thereof. For example, PHB has a melting point of 180° C. versus a melting point of about 60° C. for P4HB. The polymers also have substantially different glass transition temperatures and mechanical properties. P4HB has a glass transition temperature of −55° C. PHB is a relatively hard brittle polymer with an extension to break of just a few percent, whereas P4HB is a strong extensible polymer with an extension to break of about 1000%. P4HB has strikingly different uses from P3HB, and copolymers of P4HB with polymers such as PLA and P3HB, as well as significantly different processing requirements.

Thus, there is currently no disclosure of how P4HB can be thermoformed, the properties of P4HB films or sheets necessary for thermoforming, the intrinsic viscosities of P4HB that can be processed by thermoforming, the loss of intrinsic viscosity upon thermoforming P4HB, the conditions necessary to thermoform P4HB, the properties of P4HB thermoforms, such as tensile strength, burst strength, elongation to break, bending strength, and tensile modulus, produced by thermoforming, or the benefits of thermoforming P4HB. There is also no disclosure of the use of P4HB thermoforming to produce laminates with desirable properties.

It is therefore an object of the present invention to provide compositions of P4HB that can be thermoformed.

It is another object of the present invention to provide a means of thermoforming P4HB.

It is a further object of the present invention to provide thermoforms of P4HB produced by thermoforming characterized by specific physical properties.

It is still another object of the present invention to provide thermoforms of P4HB produced by injection molding with enhanced mechanical properties and controlled degradation profiles that can be used in medical applications.

It is yet a further object of the invention to provide laminated thermoforms with P4HB films and sheets, and methods to produce such laminates.

SUMMARY OF THE INVENTION

Methods to produce thermoforms including P4HB have been developed. These thermoforms are produced from films and sheets including P4HB, wherein the intrinsic viscosity of the P4HB is less than 3.5 dl/g, but greater than 0.35 dl/g, and the thermoforms are produced at a temperature equal to or greater than the softening point of P4HB, and more preferably at a temperature higher than the melting point of P4HB. A preferred embodiment includes a P4HB thermoform wherein a film or sheet including a P4HB polymer is thermoformed at a temperature between its melting point and 150° C. In a particularly preferred embodiment the thermoform is a laminate made from a P4HB film and a P4HB mesh.

BRIEF DESCRIPTION OF THE DRAWINGS

FIG. 1 shows the chemical structure of poly-4-hydroxybutyrate.

DETAILED DESCRIPTION OF THE INVENTION

Definitions

"Bioactive agent" is used herein to refer to therapeutic, prophylactic or diagnostic agents, such as agents that promote healing and the regeneration of host tissue and therapeutic agents that prevent, inhibit or eliminate a disease or disorder.

"Bioceramic" means a ceramic suitable for use or replacement in the human body.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed two or more different monomers.

"Burst strength" as used herein is determined, unless otherwise specified, according to ASTM D6797-02 (Standard Test Method for Bursting Strength of Fabrics Constant-Rate-of-Extension (CRE) Ball Burst Test) at ambient conditions using a ball burst fixture with a 1.6 cm circular opening and a 1 cm diameter half-rounded probe.

"Ceramic" means an inorganic, nonmetallic solid prepared by the action of heat and subsequent cooling.

"Copolymers of poly-4-hydroxybutyrate" as generally used herein means any polymer including 4-hydroxybutyrate with one or more different hydroxy acid units.

"Implant" as generally used herein include medical devices that are used in vivo as well as those that contact the surface of the body or are inserted into any orifice of the body.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer including 4-hydroxybutyrate units. It may be referred to herein as P4HB or TephaFLEX® biomaterial (manufactured by Tepha, Inc., Lexington, Mass.).

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Softening Point" as used herein means the Vicat softening point determined according to test method ASTM D1525-09. The softening point is measured as the temperature at which a polymer is penetrated to a depth of 1 mm by a flat-ended needle with a 1 sq mm circular or square cross-section under a load of 9.81 N.

"Thermoforming" as used herein refers to a method for preparing a shaped, formed article from a thermoplastic sheet, film, or similar construction. In thermoforming the sheet, film, or similar construct is heated, stretched over a mold or substance, and held in place until it solidifies. Thermoforming includes vacuum forming, pressure forming, twin-sheet forming, drape forming, free blowing, simple sheet bending, etc.

I. Composition

Methods have been developed to prepare thermoforms from sheets and films including P4HB at temperatures at or above the softening point of P4HB, and more preferably at or above the melting temperature of P4HB. These thermoforms may be used as biocompatible implants, or may be converted to biocompatible implants through further processing.

A. P4HB Homopolymer

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure as shown in FIG. 1.

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, biodegradability and relative ease of production.

Chemical synthesis of P4HB has been attempted, but it has been impossible to produce the polymer with a sufficiently high molecular weight that is necessary for most applications, including melt processing (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods.

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering. U.S. Pat. Nos. 8,034,270, 8,016,883, 8,287,909, WO 2011/119742 and WO 2011/159784 disclose fibers, non-wovens, and textiles made by melt extrusion of P4HB.

The processes described herein are used with poly-4-hydroxybutyrate (P4HB). P4HB homopolymer can be obtained from Tepha, Inc. of Lexington, Mass., USA. The P4HB homopolymer can have a weight average molecular weight, Mw, within the range of 50 kDa to 1,200 kDa (by GPC relative to polystyrene) and more preferably from 100 kDa to 1000 kDa and even more preferably from 100 kDa to 600 kDa. The polymer may include the P4HB homopolymer blended with other absorbable polymers.

Other absorbable polymers include, but are not limited to, poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); polyhydroxylkanoates (including PHB, PHBV, and P4HB copolymers); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO) or other hydrophilic or water soluble polymers such as polyvinyl pyrrolidones (PVP); polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); with blocks of other biocompatible or biodegradable polymers, for example, poly(lactide), poly(lactide-co-glycolide, or polycaprolcatone or combinations thereof.

In a preferred method, the P4HB polymer and blends of P4HB may be converted into pellets prior to making film or sheet suitable for thermoforming. Pellets may be compounded by metering in the desired ratio of polymers into a single or twin-screw extruder, wherein they are mixed prior to being extruded into pellets. The P4HB polymer and blends of P4HB may also be used in powder or granular form.

In a particularly preferred embodiment, the P4HB polymer pellets or granules that are used to prepare the film or sheet for thermoforming have intrinsic viscosities ranging from 0.35 to 3.5 dl/g. The intrinsic viscosity of the P4HB polymer may be determined using an Agilent 1100 Series HPLC equipped with an Agilent triple detector system (Agilent 390-LC Multi Detector Suite). The triple detector is equipped with a laser light scattering (LS) detector, a refractive index (RI) detector and a viscosity (Vis) detector. Samples of polymer may be prepared at 1 mg/ml in chloroform, and 100 μl of the solutions injected onto a Polymer Labs, PLgel column (5 micron, mixed C, 300×7.5 mm), and eluted at 1 ml/min. Intrinsic viscosity values may be determined using the Cirrus™ GPC/Multi Detector Software.

B. Incorporation of Additives into P4HB and Blends Thereof

Certain additives may be incorporated into the P4HB homopolymer and P4HB blends prior to converting these compositions into films or sheets. Preferably, these additives are incorporated during the compounding process to produce the pellets for extrusion into films and sheets. In another embodiment, these additives may be incorporated using a solution-based process, for example, film or sheet may be cast from solutions including P4HB and additives. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB homopolymer or P4HB blend. Such agents may be used to improve the mechanical properties of the films, sheets, and resulting thermoforms, and to reduce cycle times. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine. Plasticizers that may be incorporated include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers or radioactive substances. These additives may also be incorporated into the P4HB homopolymer and P4HB blend either before preparing the sheets or films for thermoforming or afterward thermoforming.

In yet another preferred embodiment, the additives are ceramics, more preferably bioceramics, and even more preferably resorbable bioceramics. Examples of resorbable bioceramics that can be incorporated into blends with P4HB include tricalcium phosphate (α and β forms of tricalcium phosphate (TCP)—with a nominal composition of $Ca_3(PO_4)_2$), biphasic calcium phosphate (BCP), hydroxylapatite, calcium sulfate, calcium carbonate, and other calcium phosphate salt-based bioceramics. Bio-active glasses may also be used. Bioactive glasses include bioactive glasses composed of $SiO_2$, $Na_2O$, $CaO$ and $P_2O_5$ in specific proportions. In a preferred embodiment, the P4HB blends comprise resorbable bioceramics with a size distribution ranging from nanoparticles to microparticles. In a preferred embodiment, the ceramics have particle sizes of less than 100 microns. In a particularly preferred embodiment, the P4HB blends include β-TCP, α-TCP or a combination thereof.

C. Incorporation of Bioactive Agents into P4HB Polymer and Blends Thereof

If desired, the P4HB homopolymer and blends of P4HB used to make the thermoforms may incorporate bioactive agents. These agents may be added during the formulation process, during pelletization, or may be added later to the films, sheets or the thermoforms.

In one embodiment, the bioactive agents, the P4HB polymer or P4HB blend, may be dissolved in a solvent or solvent system in order to disperse the bioactive agent in the P4HB polymer or blend, and the solvent may then be removed by evaporation. Preferred solvents include methylene chloride, chloroform, tetrahydrofuran, acetone, dimethylformamide, and 1,4-dioxane.

Examples of bioactive agents that can be incorporated into the P4HB polymer or blends of P4HB polymer, include, but are not limited to, physiologically or pharmacologically active substances that act locally or systemically in the body. Bioactive agents include biologically, physiologically, or pharmacologically active substances that act locally or systemically in the human or animal body. Examples can include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, growth factors, fibronectin, laminin, vitronectin, integrins, antibiotics, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, lipoproteins, hyaluronic acid and derivatives thereof, allograft material, xenograft material, ceramics, nucleic acid molecules, antisense molecules, aptamers, siRNA, nucleic acids, and combinations thereof.

II. Methods of Preparing Films and Sheets Including P4HB

The P4HB polymer or P4HB blend may be converted into sheet or film by any suitable method, including extrusion, solvent casting, injection molding and compression molding. In a preferred method the sheet or film including P4HB is extruded either directly from a powder or granular form, or even more preferably from pellets including P4HB.

In a particularly preferred method, powder, granules or pellets including P4HB are dried prior to melt extrusion in order to limit the loss of intrinsic viscosity of the polymer during film and sheet formation. The specific extent of drying necessary depends on the loss of intrinsic viscosity that can be tolerated for a particular application. In an embodiment, the polymer or blend to be melt-extruded is dried such that the moisture content of the polymer or blend is no greater than 0.5% by weight as measured gravimetrically, and more preferably no greater than 0.05% by weight. The polymer or blend may be dried in vacuo. In a particularly preferred method, the polymer or blend is dried in a vacuum chamber under a vacuum of at least 10 mbar, more preferably of at least 0.8 mbar, to a moisture content of less than 0.03% by weight. Elevated temperatures below the melting point of the polymer pellets may also be used in the drying process. Alternatively, the polymer may be dried by extraction into a solvent and re-precipitation, or with the use of desiccants. The moisture content of samples including P4HB may be determined using a VaporPro Moisture Analyzer from Arizona Instruments, or similar instrument, as follows. Samples should be transferred to test vials in a low humidity environment (<5% RH) to minimize pickup of ambient moisture. Samples (1 g) can then be heated to 120° C. under a purge of dry nitrogen. The moisture content of the purge gas is determined by the Vapor Pro and reported as a % of the sample weight.

Melt-extrusion may be used to prepare films of P4HB, suitable for thermoforming, using barrel and T-die temperatures of 80 to 250° C., and more preferably 100 to 220° C. In a preferred embodiment, the molten P4HB film exiting the T-die is chilled by casting it over one or more rotating cylindrical cast rollers with a surface temperature of 5 to 100° C., and more preferably 5 to 20° C. The solidified film may then be wound up in a take up step to collect the film. Films and sheets of P4HB with different thicknesses can be produced using this process by adjusting the gap of the T-die slit, and altering the polymer flow rate and cast roll speed.

Films of P4HB suitable for thermoforming may also be prepared by extrusion using an inflation method wherein an inflation molding circular die is used instead of a T-die to extrude cylindrical film. After exiting the circular die, the molten cylindrical film is cooled by blowing it up using cold air blown from the central portion of the circular die. Once the polymer has solidified, the film may be collected using a take-up machine. P4HB films and sheets of different thicknesses can be produced by changing the gap of the inflation die slit, as well as altering the polymer flow rate, cooling air pressure, temperature of the air, and the take-up speed.

In addition to melt extruding and blowing films and sheets of P4HB, suitable films and sheets for thermoforming may also be made by compression molding. In one embodiment, compositions including P4HB may be pressed into films and sheets using a Carver hydraulic press. In a preferred embodiment, compositions including P4HB powder, granules or pellets can be pressed into films and sheets by heating the platens of the press to 115° C., and pressing the P4HB composition between two sheets of mylar using metal spacers. After pressing, the film or sheet is removed from the press, allowed to cool and solidify, and removed from the mylar backing material. The thickness of the metal spaces may be adjusted in order to produce films and sheets of the desired thickness.

Films and sheets including P4HB, suitable for thermoforming, can also be prepared by solvent casting. In a preferred embodiment, a solution of P4HB can be prepared by dissolving the P4HB polymer in a solvent at a concentration of 10-15 wt/vol %, or at a concentration such that the P4HB solution has a viscosity of 400 to 7,400 cP. Suitable solvents include tetrahydrofuran, 1,4-dioxane, acetone, chloroform, and methylene chloride. The polymer solution is pumped through a slot die onto a moving web such as, for example, an aluminum foil. The distance traveled by the moving web before being taken up on a collection roller is adjusted to ensure evaporation of the solvent, and one or more air-drying zones, preferably with elevated temperatures, may be used to speed up solvent evaporation. In one embodiment, the slot die has a width of 150 mm and a 400 μm die gap, and the web speed is 0.5 m/min with the web traveling 5 m before the film is collected on a final roll. The pump speed, die gap and width, polymer concentration, and web speed may all be varied to produce P4HB films and sheets of the desired thickness and widths.

The films and sheets of P4HB may be oriented. Suitable methods to orient P4HB films and sheets include roll stretching and/or stretching with a tenter frame. In a preferred embodiment, the films and sheets are stretched at a temperature between room temperature and 150° C., more preferably at 40 to 80° C., and with a stretch ratio of 0.25 to 15. The films and sheets may be monoaxially stretched to form monoaxially-oriented films and sheets, consecutively stretched in biaxial directions to form biaxially oriented films and sheets, or simultaneously biaxially stretched to form plane-oriented films and sheets.

In a preferred embodiment, the oriented films and sheets including P4HB can be heat set to minimize or eliminate shrinking during thermoforming. Films including P4HB may be heat set by restraining the films at the desired stretched dimensions, and heating to a temperature of less than 60° C., and more preferably 35 to 45° C.

In another embodiment, the films or sheets including P4HB can be porous or fibrillated. These films or sheets can be made by mechanical or laser drilling, punching or any similar method to create pores in the film or sheet.

As well as thermoforming films and sheets made from blends of P4HB, the thermoforms may also be made from multi-layered and coextruded materials that include P4HB in one or more layers or as a co-extruded component. In a preferred embodiment these multi-layered and coextruded materials include other biocompatible materials, preferably absorbable materials, and can include additives and bioactive agents described above. In a particularly preferred embodiment, films and sheets including P4HB may be thermoformed with fibers, meshes, non-woven textiles, woven textiles, braids, tubes, films or molded forms. In an even more preferred embodiment, films and sheets including P4HB may be thermoformed with monofilament knitted meshes.

III. Thermoforming of P4HB Homopolymer and Blends Thereof

U.S. Pat. No. 8,227,060 to Obuchi et al discloses thermoforming of degradable lactic acid polymers, and teaches thermoforming of these polymers at temperatures between the glass transition temperature and melting temperature of these polymers. EP 1,136,510 to Datta and Siegmann also discloses thermoforming of degradable lactic acid polymers, and teaches that thermoforming at high temperatures will result in the film or sheet sagging under its own weight as well as loss of mechanical properties. Contrary to these teachings, it has been discovered that films and sheets including P4HB can be thermoformed at temperatures between the melting point of P4HB and 150° C. More preferably, the films and sheets including P4HB are thermoformed at temperatures of about 60° C. (the melting temperature of P4HB) and 110° C. No sagging of the sheet or films including P4HB is observed at these temperatures, and good retention of mechanical properties can also be achieved.

The thermoforms may be made using a variety of thermoforming techniques. The films and sheets including P4HB, or multi-layer sheets, may be heated, for example, in an oven (from the top, bottom, or both sides as in sandwich heating), and then molded, or these two steps may be automated and performed sequentially. In a preferred embodiment, precut films or sheets including P4HB are loaded into a clamping frame, moved into a heating chamber, and then molded. Alternatively, the films and sheets may be thermoformed in a continuous process by feeding a roll of film or sheet, including feeding film or sheet directly from an extrusion or casting line, to an automated heating/forming setup.

The method to heat the films, sheets or multilayer sheets may be selected based on the specific thermoforming technique selected, however, particularly preferred methods to heat the film are by radiation heating (for example, with a ceramic heater) or by bringing the article to be thermoformed directly into contact with a heated metal plate or the like. The heating time will depend upon the heating method selected, however, a period of time necessary to heat the film, sheet or multilayer sheets to at least the softening temperature of P4HB and more preferably the melting temperature of P4HB is required prior to forming. In an embodiment, the heating time when radiation heating is used in the thermoforming process is in the range of 1 second to 10 minutes, and more preferably 1 second to 1 minute. In another embodiment, the heating time when a metal plate is used in the thermoforming process is 1 second to 5 minutes, and more preferably 1 second to 1 minute, when the temperature of the metal plate is in the range of 60° C. to 200° C. In a preferred embodiment, the films and sheets of P4HB are preheated to 51.9° C. to 150° C. prior to thermoforming, and even more preferably 60° C. to 110° C.

The P4HB polymer and blends thereof maybe thermoformed with any thermoforming technique, including: straight forming with vacuum, straight forming with pressure, snapback forming, forming with a billow snapback, drape forming, plug-assist forming, plug-assist reverse-draw forming, air-slip forming, plug-assist air slip forming, and matched-die forming. In an embodiment, films and sheets including P4HB are thermoformed using vacuum forming, vacuum pressure forming, hot plate pressure forming or press forming by bringing the film or sheet into contact with a mold preset at a specific temperature. In another embodiment, the films and sheets including P4HB are preheated in advance, and then brought into contact with a mold preset at a specific temperature, and formed under vacuum, under pressure or under vacuum and pressure, optionally using a plug assist. In a particularly preferred embodiment, the films and sheets of P4HB are preheated to 51.9° C. to 150° C., more preferably 60° C. to 110° C., and then brought into contact with a mold preset at a temperature of 35° C. to 150° C., and more preferably 35° C. to 120° C. When a plug assist is used in the thermoforming process, the plug may also be heated to a preset temperature, preferably 35° C. to 150° C., and more preferably 50° C. to 110° C. In a further embodiment, the films and sheets including P4HB may be pre-stretched or pre-blown prior to molding.

The cycle time of the thermoforming process is controlled by the heating and cooling rates which depend on the: temperature of the heaters, cooling medium, initial temperature of the sheet, effective heat transfer coefficient, sheet thickness, and thermal properties of the film or sheet material including P4HB. The cooling time after molding is preferably as short as possible, however, it must be of sufficient duration to allow the thermoformed product including P4HB to adequately solidify so the product can be removed from the mold without its integrity being compromised. In an embodiment, the cooling time after molding is less than 15 minutes, more preferably less than 10 minutes, and more preferably less than 5 minutes. In a particularly preferred embodiment, the film and sheets including P4HB further include nucleant to increase the rate of crystallization and solidification of the thermoformed product.

In a typical procedure for thermoforming film including P4HB, a film with a thickness ranging from 0.0005 mm to 5.0 mm is loaded into a clamping frame. The film is heated to at least 51.9° C., more preferably above 60° C., and even more preferably up to 110° C., using radiant heat for up to 10 minutes, but more preferably less than 6 minutes. The heated film including P4HB is then placed over the desired mold, and pulled or pushed into place by means of a vacuum or by using an applied pressure. Alternatively, the film is stretched using a plug-assist to partially preform the product before forming is completed using vacuum and/or pressure. The thermoform is allowed time to cool and solidify before being ejected or removed from the mold.

The thermoforms including P4HB may be subsequently annealed at temperatures preferably above ambient and below 60° C., and more preferably of 45-55° C. In a preferred embodiment, the thermoforms are heated in a water bath.

In another embodiment, additional layers of film or sheet including P4HB may be thermoformed with a composite manufactured by thermoforming lamination using a sheet or film including P4HB to make a multi-layered product.

IV. Medical Implants of Thermoforms Including P4HB

Implants made from thermoforms of P4HB polymer and P4HB blends have substantially improved properties for many medical applications relative to the same compositions made from brittle degradable thermoplastics. In particular, these implants have improved toughness that prevents breakage of the implant either during implantation or prior to the conclusion of healing. Thermoforming of compositions including P4HB also allows highly oriented implants of P4HB to be prepared which is particularly advantageous when orientation is necessary in more than one direction of the implant.

Implants made from thermoforms including P4HB polymer, and blends including P4HB, may be used for soft and hard tissue repair, regeneration, and replacement. Implants made from thermoforms of P4HB polymer and P4HB blends may be used in the following medical devices, including, but not limited to, wound healing device, bandage, patch, wound dressing, burn dressing, ulcer dressing, skin substitute, hemostat, tracheal reconstruction device, organ salvage device, pledgets, dural substitute, dural patch, nerve guide, nerve regeneration or repair device, hernia repair device, hernia mesh, hernia plug, device for temporary wound or tissue support, tissue engineering scaffold, guided tissue repair/regeneration device, laminated knitted, woven and non-woven meshes, fixation devices for meshes, anti-adhesion membrane, adhesion barrier, tissue separation membrane, retention membrane, catheter, sling, device for pelvic floor reconstruction, urethral suspension device, device for treatment of urinary incontinence, device for treatment of vesicoureteral reflux, bladder repair device, sphincter muscle repair device, bulking or filling device, bone marrow scaffold, clip, clamp, screw, pin, locking pin, nail, tube, medullary cavity nail, bone plate, interference screw, tack, arrow, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, vertebral disc, cage, device for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

The implants may be made directly in the molding process, or thermoform stock may be produced that can be machined, cut, drilled, or otherwise converted into the desired device. In a particularly preferred embodiment, highly oriented thermoforms of P4HB are manufactured, and used directly as implants or after machining into implants. For example, implants that can be machined from thermoform stock including P4HB include, but are not limited to, orthopedic devices (such as pins, rods, nails, anchors, cages, vertebral discs, screws, and plates for soft and hard tissue fixation); tissue engineering structures (such as scaffolds for in vivo and in vitro tissue growth, augmentation and repair); and surgical devices (such as staples, arrows, pledgets, clamps, hooks, buttons, snaps, valves, and clips).

In a preferred embodiment, laminated implants made from films including P4HB and fibers, meshes, non-woven textiles, woven textiles, braids, tubes, films or molded forms can be prepared by thermoforming. Films including P4HB may be laminated with fibers, meshes, non-woven textiles, woven textiles, braids, tubes, films or molded forms by using vacuum, air pressure, or molds to force the heated film including P4HB together with these other components. In a particularly preferred embodiment, thermoforming lamination is used to prepare a laminate of a P4HB film and a knitted monofilament P4HB mesh. Surprisingly good adhesion between the laminate components can be achieved when the thermoforming temperature is above the melting temperature of P4HB, preferably at temperatures above 75° C., and more preferably at temperatures above 90° C. Furthermore, these laminates can be prepared without any significant loss in the mechanical strength of the oriented fibers of P4HB in the mesh, which is unexpected since exposure of the fibers in the P4HB mesh to elevated temperatures causes relaxation and loss of tensile properties.

The present invention will be further understood by reference to the following non-limiting examples.

Example 1: Thermoforming of P4HB Homopolymer

A sheet of poly-4-hydroxybutyrate with a thickness of 2.25 mm was secured in a frame. The frame including the P4HB sheet was placed into a circulating air oven, and the P4HB sheet was heated at 75° C. for 6 minutes. The softened P4HB sheet secured in the frame was then placed over an ASTM D-638 Type V tensile bar dog bone mold, and drawn down using a 200 Pa vacuum pump. The vacuum was applied for 4 seconds, and the thermoformed sheet of P4HB allowed to cool and solidify. Once the thermoformed sheet had cooled and solidified, the thermoform was removed from the frame, and the edges were trimmed. The thickness of the thermoformed P4HB was 1.56 mm. The tensile properties of the thermoformed P4HB are shown in Table 1.

TABLE 1

Tensile properties of P4HB thermoform prepared in Example 1

| Width mm | Thickness mm | Break Load N | Tensile Strength MPa | Elongation at Break % | Modulus MPa |
|---|---|---|---|---|---|
| 3.08 | 1.56 | 193.0 | 40.2 | 946.2 | 73.8 |

Example 2: Thermoforming Lamination of a P4HB Monofilament Mesh

Composite structures including a poly-4-hydroxybutyrate monofilament warp knit mesh (pore size 0.258 mm$^2$) laminated to a poly-4-hydroxybutyrate film were prepared using an American Plastics Machinery thermoforming machine, model number CRF/Recip equipped with a 6⅜"×8⅜" vacuum box with the settings shown in Table 2. In each case, P4HB mesh ($M_w$ 356 kDa) was placed inside the vacuum box on a perforated tray/board, and the vacuum box raised into place such that the heated film was forced into the mesh by the vacuum. The unoriented film ($M_w$ 414 kDa) had a thickness of 35 μm, and was heated to a temperature of 100±5° C.

The adhesion between the film and the mesh was very strong such that it was not possible to peel the film from the mesh without damaging the mesh and tearing the film. There was no apparent change in the weight average molecular weight of the film or mesh during the lamination process.

The thickness, areal density, and ball burst strength of the mesh before and after thermoforming with the P4HB film were determined, and the results are shown in Table 3. Notably, there was no apparent change in the measured thickness of the laminated mesh because the thin film had been stretched thin and drawn into the pores of the mesh. Furthermore, there was no significant loss in the mechanical properties of the mesh (e.g. ball burst strength) due to exposure of the mesh to the heat of the film. This is particularly surprising since when the mesh is exposed to elevated temperatures of greater than 65° C., the mesh can relax and contract resulting in loss of mechanical strength.

TABLE 3

Properties of P4HB thermoform laminate vs mesh prepared in Example 2

| Material | Thickness mm | Areal Density g/m$^2$ | Ball Burst Strength (Peak Load) Kgf |
|---|---|---|---|
| P4HB Mesh | 0.61 | 147.2 | 25.8 |
| P4HB Mesh Laminate | 0.61 | 193.9 | 24.3 |

The mesh laminate was further subjected to a pseudo sterilization cycle by exposing samples to a temperature of 47° C. and relative humidity of 70% for 16 hours. These conditions did not have any detrimental effect on the dimensional properties of the mesh laminate.

Example 3: Determination of Vicat Softening Point of P4HB

The Vicat softening point of a sample of poly-4-hydroxybutyrate was determined according to test method ASTM D1525-09 and found to be 51.9° C.

Example 4: Thermoforming Lamination of a P4HB Monofilament Mesh with No Perforated Tray Composite structures including a poly-4-hydroxybutyrate monofilament warp knit mesh (pore size 0.258 mm$^2$) laminated to a poly-4-hyudroxybutyrate film were prepared using an American Plastics Machinery thermoforming machine, model number CRF/Recip equipped with a 6⅜"× 8⅜" vacuum box with the settings shown in Table 2. In each case, P4HB mesh (Mw 356 kDa) was placed inside the vacuum box on a solid board slightly smaller than the mesh that left a small perimeter gap between the box and board. When the vacuum box was raised into place, the heated film sealed the edges of the vacuum box and was drawn by vacuum from the perimeter gap into the mesh. The unori-

TABLE 2

Conditions for lamination of P4HB mesh with P4HB film

| Sample | Timing Parameters | | | | | | | Temperatures | | | |
|---|---|---|---|---|---|---|---|---|---|---|---|
| | T0 | T1 | T2 | T3 | T4 | T11 | T12 | Z10 | Z11 | Z14 | Z15 |
| P4HB | 335 | 100 | 5000 | 100 | 2000 | 10000 | 300 | 1200 | 1200 | 1200 | 1200 |

T0: Length of heating time, T1: Platen delay time (bed up), T2: Part cooling delay, T3: Vacuum delay time, T4: Vacuum length, T11: Cooling time, T12: Time delay for fan on.
(Numbers: 1000 = 10 s).

ented film (Mw 414 kDa) had a thickness of 35 µm, and was heated to a temperature of 100±5° C.

The adhesion between the film and the mesh was very strong such that it was not possible to peel the film from the mesh without damaging the mesh and tearing the film. There was no apparent change in the weight average molecular weight of the film or mesh during the lamination process.

The thickness, areal density, and ball burst strength of the mesh before and after thermoforming with the P4HB film were determined, and the results are shown in Table 3. Notably, there was no apparent change in the measured thickness of the laminated mesh because the thin film had been stretched thin and drawn into the pores of the mesh. Furthermore, there was no significant loss in the mechanical properties of the mesh (e.g. ball burst strength) due to exposure of the mesh to the heat of the film.

The mesh laminate was further subjected to a pseudo sterilization cycle by exposing samples to a temperature of 47° C. and relative humidity of 70% for 16 hours. These conditions did not have any detrimental effect on the dimensional properties of the mesh laminate.

We claim:

1. A method of forming an implant comprising a thermoform of poly-4-hydroxybutyrate (P4HB) homopolymer comprising heating a single layer P4HB film or sheet to at least its softening point; and molding the heated single layer P4HB film or sheet by pneumatic or mechanical means or combinations thereof to make the thermoform.

2. The method of claim 1, wherein the single layer P4HB film or sheet is heated to at least its melting point wherein the melting point of the P4HB is about 60° C.

3. The method of claim 1, wherein the single layer P4HB film or sheet is heated to at least its melting point and molded by pneumatic or mechanical means or combinations thereof to make the thermoform, wherein the melting point of the P4HB is about 60° C.

4. The method of claim 1, wherein the P4HB has a weight average molecular weight of at least 20,000 Da and a crystallinity of at least 10%, and wherein the single layer P4HB film or sheet before the heating step has an elongation to break of at least 10%, a tensile strength of at least 20 MPa, and a tensile modulus of less than 2 GPa.

5. The method of claim 1, wherein the P4HB is produced by a microorganism or enzymatic process.

6. The method of claim 1, wherein the thickness of the single layer P4HB film or sheet is between 0.0005 mm and 5 mm.

7. The method of claim 1, wherein the weight average molecular weight of the P4HB homopolymer decreases by less than 25% upon heating and molding.

8. The method of claim 1, wherein the single layer P4HB sheet or film is heated and molded at a temperature between 60° C. and 150° C.

9. The method of claim 1, wherein before the heating step, the single layer P4HB film or sheet is unstretched.

10. The method of claim 1, wherein the single layer P4HB film or sheet is restrained in at least one direction prior to thermoforming and optionally, film is oriented in one or more directions during thermoforming.

11. The method of claim 1, wherein the implant is selected from the group consisting of patches, wound healing device, bandage, wound dressing, burn dressing, ulcer dressing, skin substitute, hemostat, tracheal reconstruction device, organ salvage device, pledgets, dural substitute, dural patch, nerve guide, nerve regeneration or repair device, hernia repair device, hernia mesh, hernia plug, device for temporary wound or tissue support, tissue engineering scaffold, guided tissue repair/regeneration device, laminated knitted, woven and non-woven meshes, fixation devices for meshes, anti-adhesion membrane, adhesion barrier, tissue separation membrane, retention membrane, catheter, sling, device for pelvic floor reconstruction, urethral suspension device, device for treatment of urinary incontinence, device for treatment of vesicoureteral reflux, bladder repair device, sphincter muscle repair device, bulking or filling device, bone marrow scaffold, clip, clamp, screw, pin, locking pin, nail, tube, medullary cavity nail, bone plate, interference screw, tack, arrow, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, vertebral disc, cage, device for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, atrial septal defect repair devices and patent foramen ovale closure devices, left atrial appendage closure device, pericardial patch, vein valve, heart valve, vascular graft, myocardial regeneration device, periodontal mesh, guided tissue regeneration membrane for periodontal tissue, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

12. The method of claim 1, wherein the P4HB homopolymer has a glass transition temperature between −45° C. and −65° C.

13. The method of claim 1, wherein before the heating step, the single layer P4HB film or sheet is mono- or biaxially stretched.

* * * * *